US007979969B2

(12) United States Patent
Basol

(10) Patent No.: US 7,979,969 B2
(45) Date of Patent: Jul. 19, 2011

(54) METHOD OF DETECTING AND PASSIVATING A DEFECT IN A SOLAR CELL

(75) Inventor: Bulent M. Basol, Manhattan Beach, CA (US)

(73) Assignee: SoloPower, Inc., San Jose, CA (US)

( * ) Notice: Subject to any disclaimer, the term of this patent is extended or adjusted under 35 U.S.C. 154(b) by 0 days.

(21) Appl. No.: 12/710,341

(22) Filed: Feb. 22, 2010

(65) Prior Publication Data
US 2010/0210040 A1  Aug. 19, 2010

Related U.S. Application Data

(63) Continuation-in-part of application No. 12/703,120, filed on Feb. 9, 2010, and a continuation-in-part of application No. 12/272,499, filed on Nov. 17, 2008.

(60) Provisional application No. 61/154,324, filed on Feb. 20, 2009.

(51) Int. Cl.
*B23P 6/00* (2006.01)

(52) U.S. Cl. ............ 29/402.06; 29/402.03; 29/825; 29/832; 29/846; 349/73

(58) Field of Classification Search .......... 29/825, 29/832, 833, 846; 349/73
See application file for complete search history.

(56) References Cited

U.S. PATENT DOCUMENTS

| 4,166,918 A | 9/1979 | Nostrand et al. |
| 4,451,970 A | 6/1984 | Izu et al. |
| 4,640,002 A | 2/1987 | Phillips et al. |
| 4,729,970 A | 3/1988 | Nath et al. |
| 4,862,000 A | 8/1989 | Kubota et al. |
| 5,677,204 A | 10/1997 | Imai et al. |
| 6,121,542 A * | 9/2000 | Shiotsuka et al. ............ 136/256 |
| 6,132,585 A | 10/2000 | Midorikawa et al. |
| 6,225,640 B1 | 5/2001 | Glenn et al. |
| 6,750,662 B1 | 6/2004 | Van Der Heide |
| 6,979,391 B1 | 12/2005 | Hubel |
| 7,117,588 B2 * | 10/2006 | Vafi et al. ................. 29/829 |
| 7,761,182 B2 * | 7/2010 | Gallarda et al. ............. 700/121 |
| RE41,603 E * | 8/2010 | Matthies ................ 349/73 |
| 2007/0227586 A1 | 10/2007 | Zapalac |
| 2008/0093221 A1 | 4/2008 | Basol |

FOREIGN PATENT DOCUMENTS

EP  1163552  3/2007

OTHER PUBLICATIONS

International Search Report issued Jan. 20, 2010 in PCT/US09/64604.

* cited by examiner

*Primary Examiner* — C. J Arbes
(74) *Attorney, Agent, or Firm* — Pillsbury Winthrop Shaw Pittman LLP

(57) ABSTRACT

The present invention provides methods of manufacturing a high efficiency solar cell. In one embodiment, in a solar cell having a grid pattern that channels current, a defect causes an undesired current flow is removed by mechanically removing a portion of the grid pattern, thereby passivating the defect by removing a segment of the solar cell adjacent the defect. The segment also includes the front and back portions of the solar cell at the location of the defect without including the defect.

13 Claims, 10 Drawing Sheets

METHOD OF DETECTING AND PASSIVATING A DEFECT IN A SOLAR CELL

CROSS REFERENCE TO RELATED APPLICATIONS

This application claims priority to U.S. Provisional Patent Application No. 61/154,324 filed Feb. 20, 2009 and this application claims priority to and is a continuation in part of U.S. patent application Ser. No. 12/703,120 filed Feb. 9, 2010, and this application is a continuation-in-part of U.S. patent application Ser. No. 12/272,499 filed Nov. 17, 2008, all of which are incorporated by reference.

BACKGROUND

1. Field of the Inventions

The present inventions relate to method and apparatus for detecting the locations of shorting defects in a thin film solar cell such as in Group IBIIIAVIA compound thin film solar cells fabricated on flexible foil substrates, and reducing the effect of such defects on the device by cutting a carefully selected section of the solar cell.

2. Description of the Related Art

Solar cells are photovoltaic devices that convert sunlight directly into electrical power. The most common solar cell material is silicon, which is in the form of single or polycrystalline wafers. However, the cost of electricity generated using silicon-based solar cells is higher than the cost of electricity generated by the more traditional methods. Therefore, since early 1970's there has been an effort to reduce cost of solar cells for terrestrial use. One way of reducing the cost of solar cells is to develop low-cost thin film growth techniques that can deposit solar-cell-quality absorber materials on large area substrates and to fabricate these devices using high-throughput, low-cost methods.

Group IBIIIAVIA compound semiconductors comprising some of the Group IB (Cu, Ag, Au), Group IIIA (B, Al, Ga, In, Tl) and Group VIA (O, S, Se, Te, Po) materials or elements of the periodic table are excellent absorber materials for thin film solar cell structures. Especially, compounds of Cu, In, Ga, Se and S which are generally referred to as CIGS-type, or CIGS(S), or Cu(In,Ga)(S,Se), or $CuIn_{1-x}Ga_x(S_ySe_{1-y})_k$, where $0 \leq x \leq 1$, $0 \leq y \leq 1$ and k is approximately 2, have already been employed in solar cell structures that yielded high conversion efficiencies. Specifically, $Cu(In,Ga)Se_2$ or CIGS absorbers have been used to demonstrate 19.9% efficient solar cells. In summary, compounds containing: i) Cu from Group IB, ii) at least one of In, Ga, and Al from Group IIIA, and iii) at least one of S, Se, and Te from Group VIA, are of great interest for solar cell applications.

The structure of a conventional Group IBIIIAVIA compound photovoltaic cell such as a $Cu(In,Ga,Al)(S,Se,Te)_2$ thin film solar cell is shown in FIG. 1. The device 10 is fabricated over a substrate 11, such as a sheet of glass, a sheet of metal, an insulating foil or web, or a conductive foil or web. The absorber film 12, which comprises a material in the family of $Cu(In,Ga,Al)(S,Se,Te)_2$, is grown on a conductive layer 13 or contact layer, which is previously deposited on the substrate 11 and which acts as the electrical contact to the device. The substrate 11 and the conductive layer 13 form a base 13A on which the absorber film 12 is formed. Various conductive layers comprising Mo, Ta, W, Ti, and stainless steel etc. have been used in the solar cell structure of FIG. 1. If the substrate itself is a properly selected conductive material, it is possible not to use the conductive layer 13, since the substrate 11 may then be used as the ohmic contact to the device. After the absorber film 12 is grown, a transparent layer 14 such as a CdS, ZnO or CdS/ZnO etc. stack is formed on the absorber film. Radiation 15 enters the device through the transparent layer 14. The transparent layer 14 is sometimes referred to as the window layer. Metallic grids (not shown) may also be deposited over the transparent layer 14 to reduce the effective series resistance of the device. The preferred electrical type of the absorber film 12 is p-type, and the preferred electrical type of the transparent layer 14 is n-type. However, an n-type absorber and a p-type window layer can also be utilized. The preferred device structure of FIG. 1 is called a "substrate-type" structure. A "superstrate-type" structure can also be constructed by depositing a transparent conductive layer on a transparent superstrate such as glass or transparent polymeric foil, and then depositing the $Cu(In,Ga,Al)(S,Se,Te)_2$ absorber film, and finally forming an ohmic contact to the device by a conductive layer. In this superstrate structure light enters the device from the transparent superstrate side. A variety of materials, deposited by a variety of methods, can be used to provide the various layers of the device shown in FIG. 1.

The conversion efficiency of a thin film solar cell depends on many fundamental factors, such as the bandgap value and electronic and optical quality of the absorber layer, the quality of the window layer, the quality of the rectifying junction, etc. A common practical problem associated with manufacturing thin film devices, however, is the inadvertent introduction of defects into the device structure. Since the total thickness of the electrically active layers of thin film solar cells is in the range of 0.5-5 micrometers, these devices are highly sensitive to defectivity. Even the micron size defects may influence their illuminated I-V characteristics. There may be different types of defects in thin film solar cell structures. Some of these defects may be only morphological in nature and they may be "nuisance defects", which are not electrically active. Other defects, on the other hand, may be electrically active and may negatively impact the performance of the device. Such defects are sometimes called "killer defects". Shunting defects, for example, may introduce a shunting path through which the electrical current of the device may leak through and therefore they may be considered to be "killer defects". Such shunting defects lower the fill factor, the voltage and the conversion efficiency of the solar cells, and therefore, they need to be minimized, eliminated or passivated. Detection and passivation of harmful defects improve the yield of thin film solar cell processing and therefore may be critical for low cost, high efficiency thin film solar cell manufacturing.

Prior work in eliminating shunting defects in solar cells includes work by Nostrand et al. (U.S. Pat. No. 4,166,918) who used an approach to bias the cell and heat up the shunts that carry a high current. A cermet material was incorporated into the cell stack which preferentially formed insulators at the shunt positions during the bias due to local heating. Izu et al. (U.S. Pat. No. 4,451,970) scanned the surface of the solar cell with a contacting liquid head which electrochemically etched or anodized the shorting regions. The etched regions could then be filled with a dielectric. This technique may be applicable for the amorphous Si type solar cells. However, etching or anodizing of CIGS type compound materials leave behind conductive residues comprising metallic species of Cu, In or Ga at the etched location that actually may make shorting even worse than before etching. Phillips et al. (U.S. Pat. No. 4,640,002) used Laser Beam Induced Current (LBIC) technique to locate shorting defects on solar cell structures and then burned the shorts out by using a high power laser beam. A similar approach is recently used in US Patent Application 2007/0227586. Hjalmar et al. (U.S. Pat.

No. 6,750,662) scanned the surface of Si solar cells with a voltage point probe and applied a voltage or light bias (illumination) detecting areas with shunts. This approach may work for thick crystalline solar cells, but would damage thin film devices. Glenn et al. (U.S. Pat. No. 6,225,640) used electroluminescence imaging on completed solar cells and removed detected defects chemically. Again such an approach is not applicable to flexible thin film devices such as CIGS cells, because as will be discussed later, defects in such thin film structures need to be detected and fixed before the solar cell is actually completed. Zapalac (US Patent Publication 2007/0227586) used laser scanning, spectroscopic ellipsometry and photoluminescence to determine shunts on finished solar cells and described ways of shunt removal by ablation or scribing.

As the brief review above shows, importance of detection and removal of shunt defects in solar cells has been recognized for many years. Much of the work has concentrated on standard Si solar cells and techniques have been developed to detect shunts in finished devices. In thin film structures using CdTe, polycrystalline Si, amorphous Si, and CIGS absorber layers, the nature and chemical composition of the layers within the device structure are widely different, changing from a single element (Si), to more complex compounds such as a binary compound (CdTe), a ternary compound (ClS), a quaternary compound (ClGS), and a pentenary compound (ClGSS). Therefore, one defect removal method which may work for one device may not work for the other. The laser ablation method that is used for shunt removal, for example, is very successful for Si devices because Si can be easily ablated without leaving behind debris that would affect device performance. For CdTe, process window for laser ablation is narrow because there is the possibility of formation of conductive debris comprising metallic Cd and/or Te at the location where laser ablation is performed. For CIGS, there is to date no successful laser ablation process because laser heating of this compound semiconductor leaves behind conductive phases comprising Cu, In, Ga metals and/or Cu—Se phases. Such conductive phases introduce further shunts in the device structure at the laser ablated locations. Similarly, techniques using chemical etching of defect areas introduce problems for devices employing compound semiconductors such as CdTe and CIGS(S). In such compounds, chemical etching does not etch the material uniformly and leaves behind conductive residue.

For example, an exemplary CIGS type solar cell may have a 100-300 nm thick transparent conductive layer, 50-100 nm thick buffer layer, 1000-2000 nm thick absorber layer and 200-500 nm thick contact layer. The substrate is typically 25-100 μm thick and the grid pattern has a thickness in the 5-50 μm range. In such thin and flexible device structures scribing over the defect with a mechanical tool peels off and damages the various device layers at the vicinity of the defect which already has a shorting path for the electrical current, and also damages the metallic substrate which is flexible and pliable. Such damage from the conducting parts of the solar cell may create conductive debris shorting the top surface of the device to the substrate, the debris originating from the damaged substrate region, the contact layer as well as the transparent conductive layer and especially the portion of the grid pattern damaged by the scribing tool. Laser approaches used to remove defects from standard solar cells also do not work well for foil based thin film devices such as CIGS type devices. First of all, adjustment of the laser power to remove only the top transparent conductive layer or the grid pattern at the defect region is very difficult, and sometimes impossible. The laser beam, by heating the grid pattern and/or the metallic substrate, may cause local melting of the metal substrate and cause new shorting defects, especially for thin film solar cell structures constructed on conductive substrates. Laser removal of CIGS itself may create conductive debris around the removal area comprising metallic species such as Cu, In, and Ga. Such conductive debris is a source of new shorting defects in the device structure. Especially the most serious shorting defects which are under the grid pattern may not be removed by laser processes.

Therefore, there is a need to develop defect detection and passivation approaches that are specifically suited for CIGS-type thin film device structures manufactured in a roll-to-roll manner.

SUMMARY

The present inventions relate to method and apparatus for detecting efficiency reducing defects in a thin film solar cell such as a Group IBIIIAVIA compound thin film solar cell, and cutting a section of the solar cell to improve its efficiency.

The present invention provides methods of manufacturing a high efficiency solar cell. In one embodiment, in a solar cell having a grid pattern that channels current, a defect causes an undesired current flow is removed by mechanically removing a portion of the grid pattern, thereby passivating the defect by removing a segment of the solar cell adjacent the defect. The segment also includes the front and back portions of the solar cell at the location of the defect without including the defect.

In different embodiments, different types of input signals can be input and corresponding output signals can be detected. For example, the input signal can induce one of infra-red (IR) radiation, photoluminescence and electroluminescence as the output signal.

BRIEF DESCRIPTION OF THE DRAWINGS

These and other aspects and features of the present invention will become apparent to those of ordinary skill in the art upon review of the following description of specific embodiments of the invention in conjunction with the accompanying figures, wherein.

DETAILED DESCRIPTION

The embodiments of the present inventions provide defect detection processes, apparatus to detect defects in solar cell structures and methods and apparatus to passivate that defect. In some embodiments, instead of passivating or removing the defect itself, its effect is reduced or eliminated by partially cutting the solar cell structure including the substrate, in predetermined locations. These methods are especially suited for flexible thin film solar cell structures built on flexible thin film substrates such as polymeric substrates and metallic substrates. Such polymeric substrates include, but are not limited to polyimide-based high temperature substrates, and the metallic substrates include but are not limited to stainless steel, titanium, molybdenum, and aluminum containing conductive substrates. The semiconductor absorber layers of such flexible substrates may include CIGS type materials, cadmium telluride type Group II-VI materials, amorphous Si, polycrystalline or microcrystalline Si, organic semiconductors, and absorber layers employed in dye-cells such as dye-titanium oxide containing layers.

In one embodiment a roll-to-roll defect detection and passivation apparatus may be used to detect and passivate the defects formed within a flexible continuous workpiece including a stack of a base, a CIGS absorber formed on the base and a transparent conductive layer formed on the CIGS absorber layer. During the process, initially a section of the continuous flexible workpiece is made substantially flat and an input signal from a signal source is applied to a front surface of the section. The front surface may be the top surface of the transparent conductive layer or a surface of a temporary layer coated on the transparent conductive layer. In response to the input signal, an output signal is generated from a predetermined area of the front surface and detected by a defect detector. The output signal carrying the defect position information is transmitted to a computer and registered in a database. With the position information, an injector device is driven to the defect location to apply an insulator material, preferably an insulating ink, to passivate the defect. If the surface has a temporary layer, the passivation process is performed after removing the temporary layer. A grid pattern layer may be formed over the predetermined area after completing the defect detection and passivation processes.

Figure 2:
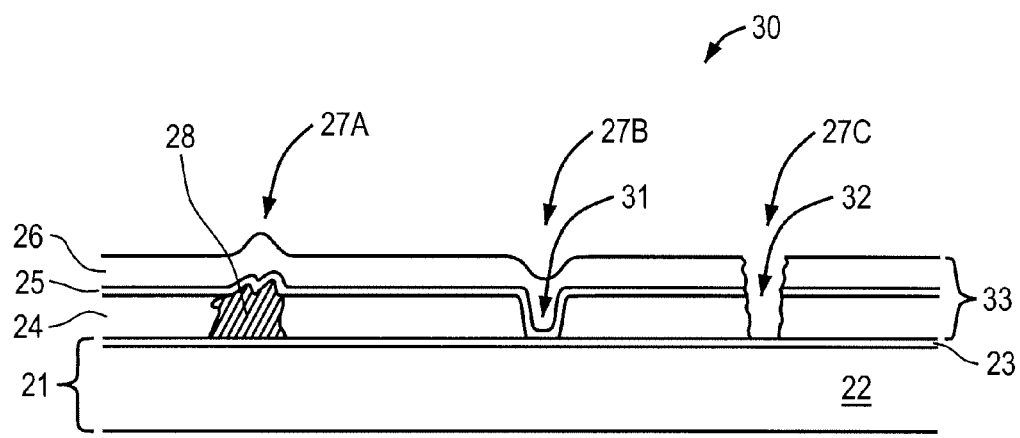
FIG. 2 shows a section of a solar cell structure with three different exemplary types of defects.

Certain aspects of the embodiments will now be described using a solar cell structure 30 shown in FIG. 2. FIG. 2 shows a cross sectional view of an exemplary section of a solar cell structure 30 with three different exemplary defect regions, 27A, 27B and 27C. The solar cell structure 30, which may be a CIGS thin film solar cell structure, comprises a base 21 which includes a substrate 22 and a contact layer 23. An absorber layer 24 or CIGS layer is formed on the contact layer 23. It should be noted that the solar cell structure 30 is only exemplary and the embodiments may be applied to many other thin film solar cell structures utilizing other solar cell absorber layers. A buffer layer 25 such as a CdS layer and a transparent conductive film 26 such as a transparent conductive oxide (TCO) film are then deposited over the CIGS layer 24. The TCO film 26 may be a ZnO film, an indium tin oxide (ITO) film, or a TCO stack film, such as an "undoped ZnO/doped ZnO" stack film or a ZnO/ITO stack film, etc.

As shown in FIG. 2, a conductive particle 28 over the contact layer 23 causes the defect region 27A to form. The conductive particle may be introduced during or before the deposition of the CIGS layer 24. Alternately, the conductive particle 28 may be inadvertently introduced during the deposition of the contact layer 23, and therefore, it may be in or under the contact layer 23. Regardless of how it may be introduced, the conductive particle 28 establishes a conductive path between the TCO film 26 and the contact layer 23. Presence of the buffer layer 25 in this conductive path may increase its resistance. However, since the thickness of the buffer layer 25 is typically less than 100 nm, it is generally not adequate to fully eliminate the conductive path between the TCO film 26 and the contact layer 23 in the defect region 27A. Defect region 27B in FIG. 2 may be formed by the presence of a pinhole 31 in the CIGS layer 24. The pinhole 31 may be formed during or after the deposition of the CIGS layer 24 and the cavity formed by the pinhole 31 may be filled by the buffer layer 25 and the TCO film 26 during subsequent process steps. Alternately the pinhole 31 may form during or after the deposition of the buffer layer 25, in which case, its cavity would be filled only by the TCO film 26. In any case, as can be seen from FIG. 2, the pinhole 31 filled by the TCO film 26 introduces a conductive path between the TCO film 26 and the contact layer 23. Presence of the buffer layer 25 in this conductive path may increase its resistance. However, since the thickness of the buffer layer 25 is typically less than 100 nm, it usually is not adequate to fully eliminate the conductive path between the TCO film 26 and the contact layer 23 in the defect region 27B. Defect region 27C in FIG. 2 may be formed by the presence of a void 32 in the "CIGS layer/buffer layer/IVO film" stack 33. The void 32 may be formed during or after the formation of the TCO film 26. The void 32 may not be filled by any conductive material, and therefore, there may not be a conductive path between the TCO film 26 and the contact layer 23 through the void 32 at the defect region 27C. In this respect, the defect region 27C may be considered a "nuisance defect" region. However, this situation may change when a finger pattern or grid pattern is deposited over the TCO film 26, as will be described next.

Figure 3:
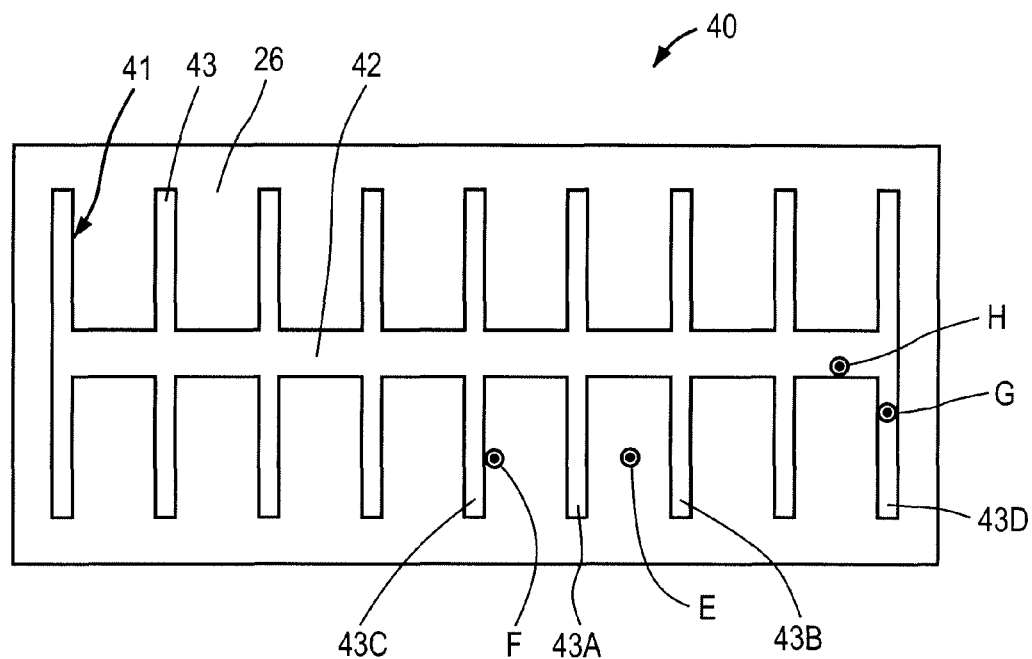
FIG. 3 shows a top view of a thin film solar cell with a grid pattern.

FIG. 3 shows a top view of an exemplary CIGS solar cell 40. The CIGS solar cell 40 may be obtained by depositing a grid pattern 41 on the TCO film 26 of the solar cell structure 30 depicted in FIG. 2. The grid pattern 41 typically comprises one or more, 1-4 mm wide busbars 42, which are the main carriers or conduits of the light generated and collected current of the device, and multiple narrow fingers 43, which may be 50-200 micrometers wide and distributed in specially designed patterns on the top surface of the TCO film 26 to collect the light generated current with minimal electrical loss and to deliver it to the busbars 42. As is well known in the field, the grid pattern 41 is designed to maximize the amount of light shining on the TCO film 26 (i.e. to minimize the shadow loss) and at the same time to minimize the overall series resistance of the solar cell 40. Finger patterns or grid patterns comprise highly conductive metals such as Ag, Ni, Cu, etc., and are deposited by techniques such as evaporation, electroplating, ink jet writing and screen printing. Ink jet writing and screen printing approaches usually employ Ag-particle based inks or pastes that are deposited on the surface of the TCO film 26 in the form of the grid pattern 41. In any case, the busbars 42 and fingers 43 are designed to be highly conductive since their purpose is to lower the series resistance of the device and transmit the current with minimal "I.R" loss. Materials employed in the structure of the grid pattern 41 have bulk resistivity values in the order of $10^{-5}$-$10^{-6}$ ohm-cm. The sheet resistance of the fingers 43 and the busbars 42 may be typically less than 0.01 ohms/square. The typical sheet resistance of the TCO film 26, on the other hand, may be in the range of 10-100 ohms/square, which is at least 1000 times larger than the sheet resistance of the grid pattern 41.

The exemplary defect regions 27A, 27B and 27C of FIG. 2 may further influence the completed device performance once the grid pattern 41 including a busbar 42 and fingers 43 is deposited on the TCO film 26 to form the solar cell 40 shown in FIG. 3. This may be shown using four exemplary locations on the solar cell 40, which are labeled as location E, location F, location G and location H.

If the exemplary defect region 27A described above was located at the location E, although it is away from the busbar 42 and between the two fingers 43A and 43B, the solar cell performance could be affected. As explained before, there is a conductive path between the TCO film 26 and the contact layer 23 at the defect region 27A. However, this shunting path can affect a small area of the solar cell 40 in the near vicinity of the location E. This is because the sheet resistance of the TCO film 26 is relatively high and the current collected by the TCO layer 26 between the finger 43A and finger 43B mostly chooses to flow towards these two fingers and the busbar 42, which have much lower resistance than the TCO film 26. Therefore, the defect region 27A at the location E may affect the solar cell performance, but it does not totally short circuit the device.

If the defect region 27A was at the exemplary location F which is next to finger 43C, its influence on the cell performance would be worse compared to the case discussed above, because the resistance between the finger 43C and the defect region 27A is much smaller due to the shorter distance between them. If the defect region 27A was at the location G or the location H, which are under the finger 43D and the busbar 42, respectively, it would greatly influence the performance of the solar cell 40. In this case, the very low resistance finger 43D and busbar 42 are directly over the defect region 27A, and thus the current collected by the finger 43D and the busbar 42 has a direct low resistance path to the contact layer 23. This is shunting and it is expected to reduce the fill factor, voltage and the conversion efficiency of the solar cell 40 greatly.

If the defect region 27B described above is at the exemplary location E, which is away from the busbar 42 and between the two fingers 43A and 43B, it may affect the solar cell performance. As explained before, there is a conductive path between the TCO film 26 and the contact layer 23 at the defect region 27B. However, this shunting path can affect only a small area of the solar cell 40 in the near vicinity of the location E. This is because the sheet resistance of the TCO film 26 is relatively high and the current collected by the TCO layer 26 between the finger 43A and finger 43B chooses to flow towards these two fingers and the busbar 42 which have much lower resistance than the TCO film 26. Therefore, the defect region 27B at the location E may affect solar cell performance, but it does not totally short circuit the device. If the defect region 27B was at the location F, which is next to the finger 43C, its influence on the cell performance could be worse compared to the case just discussed, because the resistance between the finger 43C and the defect region 27B is much smaller due to the shorter distance between them. If the defect region 27B was at the location G or the location H, which are under the finger 43D and the busbar 42, respectively, it would greatly influence the performance of the solar cell 40. In this case, the very low resistance finger 43D and busbar 42 are directly over the defect region 27B, and thus the current collected by the finger 43D and the busbar 42 has a direct low resistance path to the contact layer 23. This is shunting and it is expected to reduce the fill factor, voltage and the conversion efficiency of the solar cell 40.

The defect region 27C described above may be at the location E, which is away from the busbar 42 and between the two fingers 43A and 43B. In this case, as explained before, there is not a conductive path between the TCO film 26 and the contact layer 23 at the defect region 27C. Therefore, the void 32 at the defect region 27C does not generate photocurrent, but it does not introduce any shunting either. Since the size of the void 32 is typically much smaller than the total area of the solar cell 40, the loss of photocurrent is usually insignificant. For example, for a 100 $cm^2$ area solar cell, a 100 micrometer diameter void introduces only 0.00008% reduction in the generated photocurrent and it does not introduce any shunt at the location E. The situation does not change even if the defect region 27C was at the location F which is next to the finger 43C, i.e. the void 32 at the defect region 27C does not generate photocurrent, but it does not introduce any shunting either. If the defect region 27C was at the location G or at the location H, which are under the finger 43D and the busbar 42, respectively, the situation changes drastically. In this case the defect region 27C may greatly influence the performance of the solar cell 40. Specifically, as the busbar 42 and the finger 43D are deposited over the TCO film 26, the conductive materials such as Ag-filled inks or pastes constituting the grid pattern material, flow into the void 32 and establish a highly conductive shorting path between the grid pattern 41 and the contact layer 23 at the locations G and H. Thus the current collected by the grid pattern 41 find a direct low resistance path to the contact layer 23. This is shunting and it is expected to reduce the fill factor, voltage and the conversion efficiency of the solar cell 40.

As the discussion above indicates, unlike in thick Si solar cells, defects in a thin film solar cell structure negatively impact the solar cell performance, especially when any section of a grid pattern is formed on such defects. Therefore, detection and passivation of such defects in the solar cell structure are needed. Such detection and passivation preferably need to be carried out before the grid pattern is deposited or formed over the cell structure, i.e. before the solar cell is fully fabricated.

In an embodiment of the present invention, a solar cell structure is first fabricated without a grid pattern. Before the grid pattern is formed on the cell structure, a defect detection process is carried out. This process identifies the locations of the defects in the solar cell structure which may or may not be shunts, but would create shunts after finger pattern deposition. A defect passivation process may then be carried out to passivate at least some of the defects that are detected. A grid pattern is then formed on the window layer.

Figure 4:
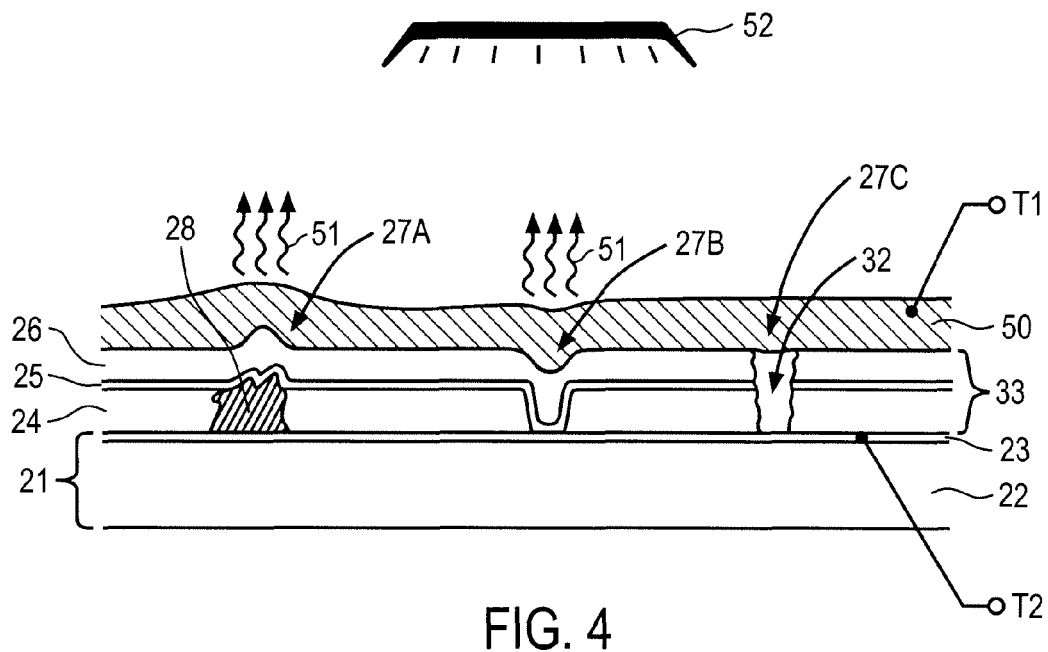
FIG. 4 shows a method of detecting defects in thin film solar cells.

FIG. 4 shows a method and apparatus to detect at least some of the defect regions that were discussed with reference to FIG. 2. As can be seen from FIG. 4, a temporary conductive blanket 50 is formed over the solar cell structure 20 of FIG. 2. In FIG. 4, the exemplary temporary conductive blanket 50 is a conductive and flexible foil such as a 10-75 micrometer thick metal foil that establishes good physical and electrical contact with the top surface of the TCO film 26. A first terminal T1 is attached to the temporary conductive blanket 50 and a second terminal T2 is attached to the contact layer 23. If the substrate 22 is a conductive foil, the second terminal T2 may be attached to the substrate 22 instead of the contact layer 23. Next, a voltage bias is applied between the first terminal T1 and the second terminal T2. It is preferable that this applied voltage biases the solar cell structure 20 in a voltage range that does not allow appreciable current passing through the device. In other words, the voltage applied either reverse biases the device or if it forward biases it, it applies a voltage that is smaller than the turn-on voltage of the diode.

Since there are conductive paths between the TCO film 26 and the contact layer 23 at the defect region 27A and the defect region 27B, however, a shunt current passes between the temporary conductive blanket 50 and the contact layer 23 through the defect regions 27A and 27B. The shunt current heats up the portions of the temporary conductive blanket 50, right over the defect regions 27A and 27B. A strategically located IR camera 52 detects the IR radiation 51 emanating from these heated defect regions. In a particular embodiment, the applied bias can be modulated and the images from the IR camera processed in such a way as to "lock-in" on the modulated signal from the shunt. This technique may yield improved shunt detection. In another embodiment, the transparent conductive blanket can be replaced with a rolling contact, or pair of rolling contacts that stretch across the width of the cell. Conductive brushes may also be utilized as a substitute for the roller. As the moving temporary contact passes over or near the shorting defect region, the region gets heated and the IR camera detects the heated defect region.

The information about the location of the shunt defects may be saved by a computer and this location information may later be used to passivate the defective regions after the temporary conductive blanket 50 is removed from the top surface of the TCO film 26. It should be noted that the exemplary temporary conductive blanket 50 of FIG. 4 is a flexible foil and it may not fill the void 32 of the defect region 27C, and therefore cannot establish an electrical short circuit with the contact layer 23 through the void 32. Consequently, no shunting current passes through the defect region 27C upon application of a voltage between the terminals T1 and T2. As a result, this defect region may go undetected. To be able to detect defects such as the one at defect region 27C, it is preferable to use a temporary conductive blanket which may be in the form of a liquid or gel. This way the material of the conductive blanket would go into the void 32 and establish a short circuit between the conductive blanket and the contact layer 23. When shorting current passes through, it would heat the defect region 27C and the IR camera, operating either in DC or AC "lock-in" mode, depending on the type of bias utilized (DC or AC) could detect this heating.

Figure 5:
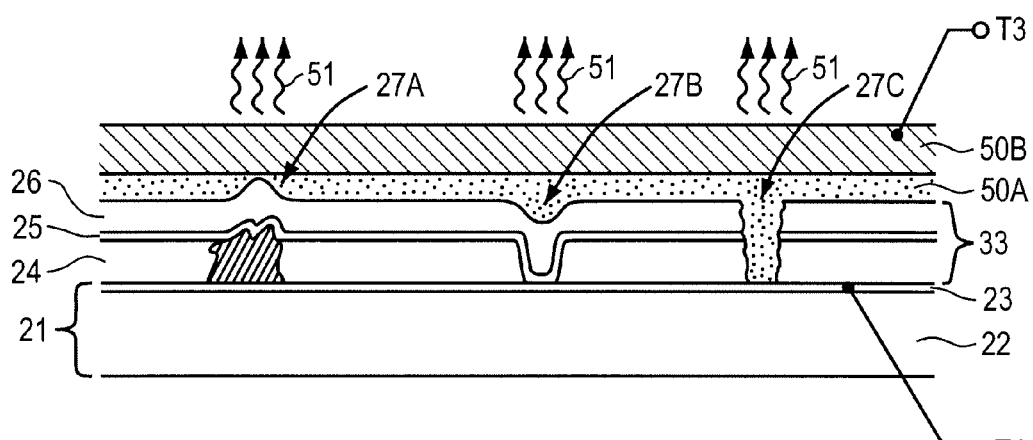
FIG. 5 is shows another method of detecting defects in thin film solar cells.

It is also possible to use a combination of different types of temporary conductive blankets. In FIG. 5, for example, a temporary conductive liquid blanket 50A is used in conjunction with a temporary conductive solid blanket 50B. The temporary conductive liquid blanket 50A may be an ionic liquid, a salt solution, etc., which has enough conductivity to allow a shunt current to pass through it but is inert and does not etch or anodize any of the solar cell layers (23, 24, 25, 26). The temporary conductive solid blanket 50B may be a thin (10-50 micrometers) metallic foil. A terminal T3 may be attached to the temporary conductive solid blanket 50B and a terminal T4 may be attached to the contact layer 23. If the substrate 22 is a conductive foil, the terminal T4 may be attached to the substrate 22 instead of the contact layer 23. Next, a voltage bias is applied between the terminal T3 and the terminal T4. It is preferable that this applied voltage biases the solar cell structure 20 in a voltage range that does not allow appreciable current passing through the device itself. However, since there are conductive paths between the TCO film 26 and the contact layer 23 at the defect regions 27A, 27B, and 27C, a shunt current passes between the temporary conductive solid blanket 50B and the contact layer 23, through the temporary conductive liquid blanket 50A and the defect regions 27A, 27B and 27C. The shunt current heats up the portions of the temporary conductive solid blanket 50B, right over the defect regions 27A, 27B and 27C. A strategically located IR camera (not shown) detects the IR radiation 51 emanating from all three defect regions. Operation in AC or "lock-in" mode may allow for the use of lower bias to achieve the same signal level for defect detection, reducing collateral damage to the cell. The information about the location of the shunt defects may be saved by a computer and this location information may later be used to passivate the defective regions after the temporary conductive solid blanket 50B and the temporary conductive liquid blanket 50A are removed from the top surface of the TCO film 26.

Figure 6:
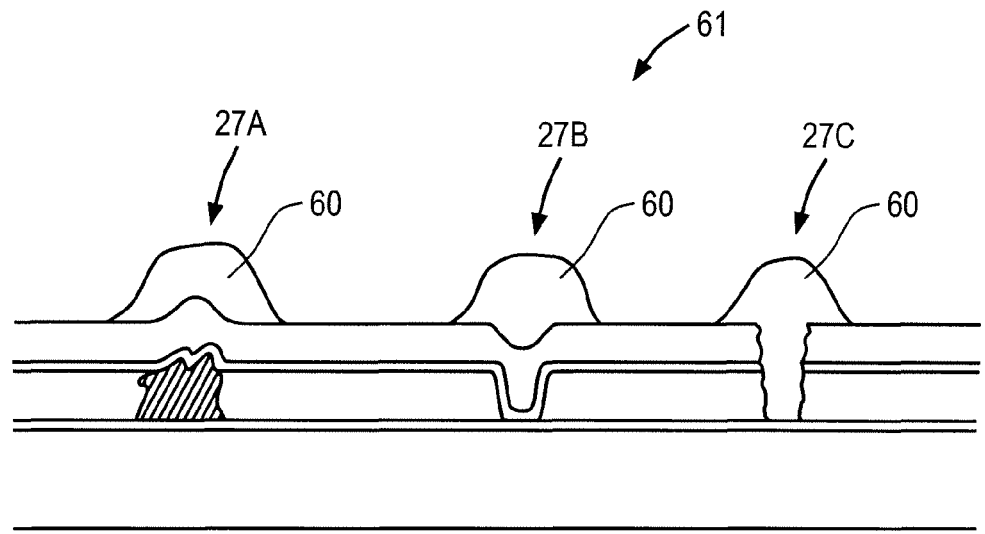
FIG. 6 shows the defects shown in FIG. 2, wherein the defects have been passivated.

After collecting the defect location information, passivation of the defect regions 27A, 27B and 27C may be achieved by forming high resistance caps 60 over them as shown in FIG. 6. The high resistance caps 60 may be applied by various ways including by small injectors or ink jet heads that may travel to the already determined position of the defect and dispense a small amount of a high resistivity material. The high resistivity material may be in the form of an ink which may be later cured by heat or radiation. Ultra violet curable insulating inks are well suited for this application since they can cure quickly within a few seconds. It should be appreciated that, formation of a grid pattern (not shown) on the defect-passivated solar cell structure 61 of FIG. 6 would not cause shorting or shunting even if the busbars or fingers of the grid pattern directly land on any of the passivated defect areas 27A, 27B and 27C.

Figure 7:
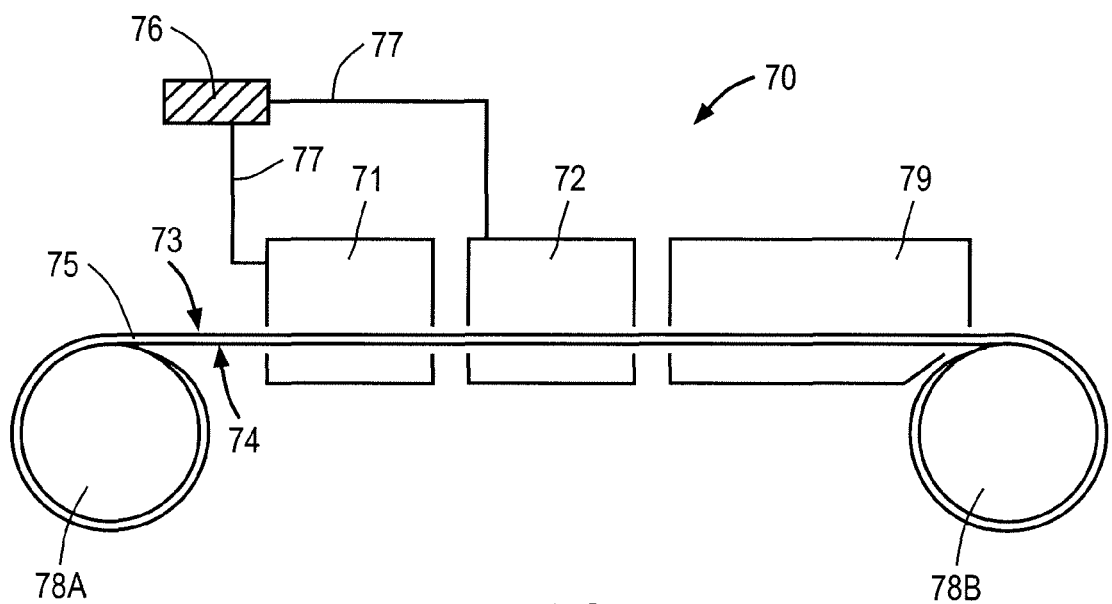
FIG. 7 shows a defect detection and passivation system.

Defect detection and passivation may be carried out on individually cut solar cell structures or they may preferably be carried out in a roll-to-roll manner on a continuous solar cell structure. FIG. 7 shows a roll to roll processing system 70 to detect and passivate defect regions on a workpiece 75 with a top surface 73 and a bottom surface 74. For example, the workpiece 75 may comprise a device structure similar to the solar cell structure 30 shown in FIG. 2. Therefore, the top surface 73 may be the top surface of the TCO film 26 and the bottom surface 74 may be the bottom surface of the substrate 22. The workpiece 75 may be fed by a supply spool 78A and may be rolled back up in a receiving spool 78B after processing. The roll to roll processing system 70 comprises at least one detection station 71 and at least one passivation station 72. As portions of the workpiece 75 travel from the supply spool 78A to the receiving spool 78B either in a continuous motion or in a step-wise motion, they pass through the detection station 71 and the passivation station. Defect regions are detected in the detection station 71, using, for example, the methods described before. A computer 76 is in communication with the detection station 71 and the passivation station 72 through cables 77. The computer 76 may also be in communication with the motion control system (not shown) that controls the motion of the workpiece 75 between the supply spool 78A and the receiving spool 78B. This way the computer 76 gathers the defect location information for a portion of the workpiece measured in the detection station 71 and provides this information to the passivation station 72 so that when that portion of the workpiece is advanced to the passivation station 72, the defect regions identified in the detection station 71 may be passivated. After the passivation of the defect areas, the defect-passivated work piece may be rolled up in the receiving spool 78B and moved to another process station. Preferably, however, the above described detection and passivation processes may be integrated with a grid pattern formation process. In this case, after defect region passivation, the portion of the defect-passivated workpiece moves into a grid application station 79 within which a grid pattern may be deposited and cured on the front surface 73. The grid application station 79 may be a screen printing station, an ink jet writing station and the like, that forms a grid pattern on the defect-passivated portion of the workpiece.

It should be noted that since the solar cell parameters are most negatively impacted by the presence of defects directly under or in close proximity of the grid pattern, defect detection and defect passivation processes may be limited only to these areas. Doing so increases the throughput of the detection and passivation processes compared to the case that carries out such detection and passivation processes over substantially the whole surface of a thin film solar cell structure. In the high throughput process, the location of the grid pattern to be deposited is predetermined and therefore the defect detection and passivation processes are applied to this predetermined location. Considering the fact that grid pattern in a typical solar cell covers only less than 10% of its total area, this approach reduces the area of defect detection and passivation by 90% and increases the throughput of these processes greatly. For example, the roll to roll processing system 70 may be used in this mode to increase its throughput by 10 times or even more. With the increased throughput it becomes feasible to integrate the roll-to-roll defect detection and passivation process with a high speed roll-to-roll finger pattern screen printing process, i.e. carrying out the screen printing step right after the detect passivation step within the same process tool.

Figure 8:
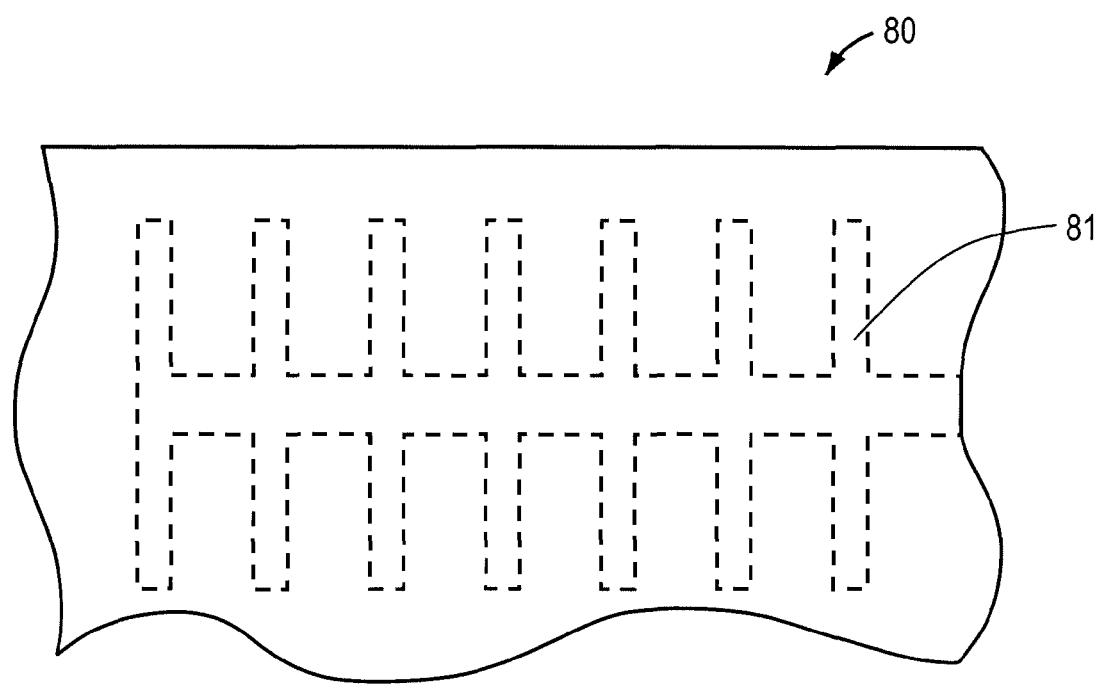
FIG. 8 shows a section of a solar cell structure with a predetermined grid region.

FIG. 8 shows a section 80 of a solar cell structure. The predetermined grid region 81 shown by the dotted lines is a region on the top surface of the section 80 of the solar cell structure, which will receive a grid pattern, such as the grid pattern 41 of FIG. 3, after the step of passivation. The predetermined grid region 81 is substantially the same shape as the grid pattern to be deposited. Preferably, the predetermined grid region 81 is somewhat larger than the grid pattern to assure that when the grid pattern is deposited it falls well within the boundaries defined by the dotted lines in FIG. 8. It is noted that the predetermined grid region 81 is less that 20$, and typically less than 10%, of the surface area for a given section. When the section 80 of the solar cell structure is processed in a defect detection station, the process of detection may be applied just to the predetermined grid region 81 finding and locating the defects only in this region, and due to the grid region 81 area being much less than the area of the entire section, as noted by the percentages above, this can allow for significant benefits. For example, if a laser scanning approach such as LBIC method is used for defect detection, the laser may be scanned only through the predetermined grid region 81 and the positions of the defects identified may be stored by a computer for future use during passivation. Of course, it would also be possible to collect a complete defect data through substantially the whole surface of the section 80 of the solar cell structure but then passivate only the defects falling within the predetermined grid region 81, thus also increasing the throughput of the passivation process. In any case, when the section 80 of the solar cell structure is advanced into a defect passivation process station, defects that fall within the predetermined grid region are passivated by forming high resistivity caps as described before. After defect passivation of the predetermined grid region 81, a grid may be deposited on the predetermined grid region 81. It should be noted that the temporary conductive blankets used for detection of defects in specific regions of a solar cell structure, such as the predetermined grid region 81 of FIG. 8, may be shaped just like that specific region.

The defect region detection methods may be non-contact or contact methods. In non-contact methods, no electrical contact needs to be made to the solar cell structure such as the solar cell structure depicted in FIG. 2. For contact methods, electrical contacts need to be made to the device to carry out a detection procedure. In contact methods one contact is made to the transparent conductive layer (layer 26 in FIG. 2) and the other one to the back contact of the device (layer 23 in FIG. 2). If the substrate is a conductive foil (see substrate 22 in FIG. 2) then the back contact may be made on the exposed back surface of the substrate itself since the substrate and the device contact layer are electrical shorted. A roll-to-roll system will now be described where both contact and non-contact methods may be applied to a flexible CIGS type solar cell structure (such as the one showed in FIG. 2) for the purpose of detecting various defects in the structure. In this example, the detection station 71 and the passivation station 72 of FIG. 7 are merged together and various different detection method examples are given.

Figure 9A:
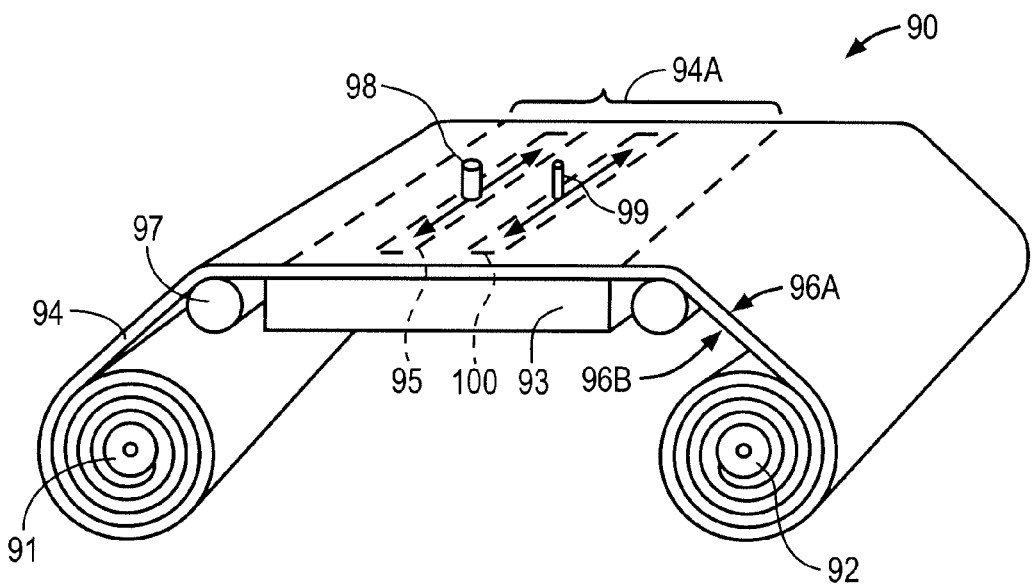
FIG. 9A shows an embodiment of a defect detection tool of the embodiments of the present invention.

A roll-to-roll defect detection and passivation system 90 is shown in FIG. 9A. As shown in FIG. 9A, the system 90 comprises a feeding roller 91, a receiving roller 92, and a process platform 93 disposed between the two rollers. A flexible and continuous workpiece 94 is fed by the feeding roller 91 and passes onto the top surface of the process platform 93 and then is rolled back up on the receiving roller 92 by a moving mechanism (not shown). The workpiece 94 includes a front surface 96A and a back surface 96B. The workpiece 94 may comprise a device structure similar to the solar cell structure 30 shown in FIG. 2. Therefore, the front surface 96A may be the top surface of the TCO film 26 and the back surface 96B may be the back surface of the substrate 22. The top surface of the process platform 93 is substantially flat and may include vacuum holes so that when a section 94A of the workpiece 94 is moved on the top surface of the process platform 93 it can be registered flat onto the top surface by applying vacuum to a portion of the back surface 96B that is on the process platform 93. Once the section 94A of the workpiece 94 is registered flat onto the top surface of the platform, defect detection and/or passivation process may be carried out at least over a predetermined portion of the section 94A, which is indicated as detection area 95 in FIG. 9A. Defect detection process may be carried out using a detector 98 which can move across the front surface of the continuous workpiece over a predetermined detection area 95 when the workpiece is at a detection location.

During the defect detection process an input signal is applied from an input signal source to the predetermined detection area, and an output signal from the predetermined area carrying the defect information is collected by the detector. Exemplary, input signals may be delivered through shining light onto the detection area, applying a voltage between the detection area 95 and the substrate of the workpiece. The output signals may be infra-red (IR) radiation, photoluminescence radiation and electroluminescence radiation and the like, each of which can be operated in DC or AC "lock-in" mode. As sections of the workpiece 94 is advanced from the supply spool 91 to the receiving spool 92 either in a continuous motion or in a step-wise motion, preferably, in a step-wise motion, defect detection is carried out in the detection area 95 and the position information of the detected defects carried by the output signal are recorded by a computer (not shown). This position information is then used to passivate the detected defects in a passivation location. When the detection area 95 moved from the detection location to the passivation location of the system by moving the workpiece 94, it becomes passivation area 100. In essence, both the detection area and the passivation area are the same predetermined area on the front surface of the section of the continuous workpiece in two different locations where the detection and passivation processes can be applied. An injector 99 which may be moved across the front surface 96A of the workpiece 94 over the passivation area 100 goes to the position where the defect has been detected and dispenses a high resistivity ink over the defect region. If the ink is heat-cured or UV-cured type, such curing means may also be applied to the deposited ink (not shown). It should be noted that the detection area 95 and the passivation area 100 may actually be the same area, i.e. both defect detection and passivation may be carried out one after another when the workpiece 94 is kept stationary. However, separating the detection and passivation steps increases throughput. In fact, for higher throughput there may be two or more detection areas with two or more detectors and two or more passivation areas with two or more injectors.

Figure 9B:
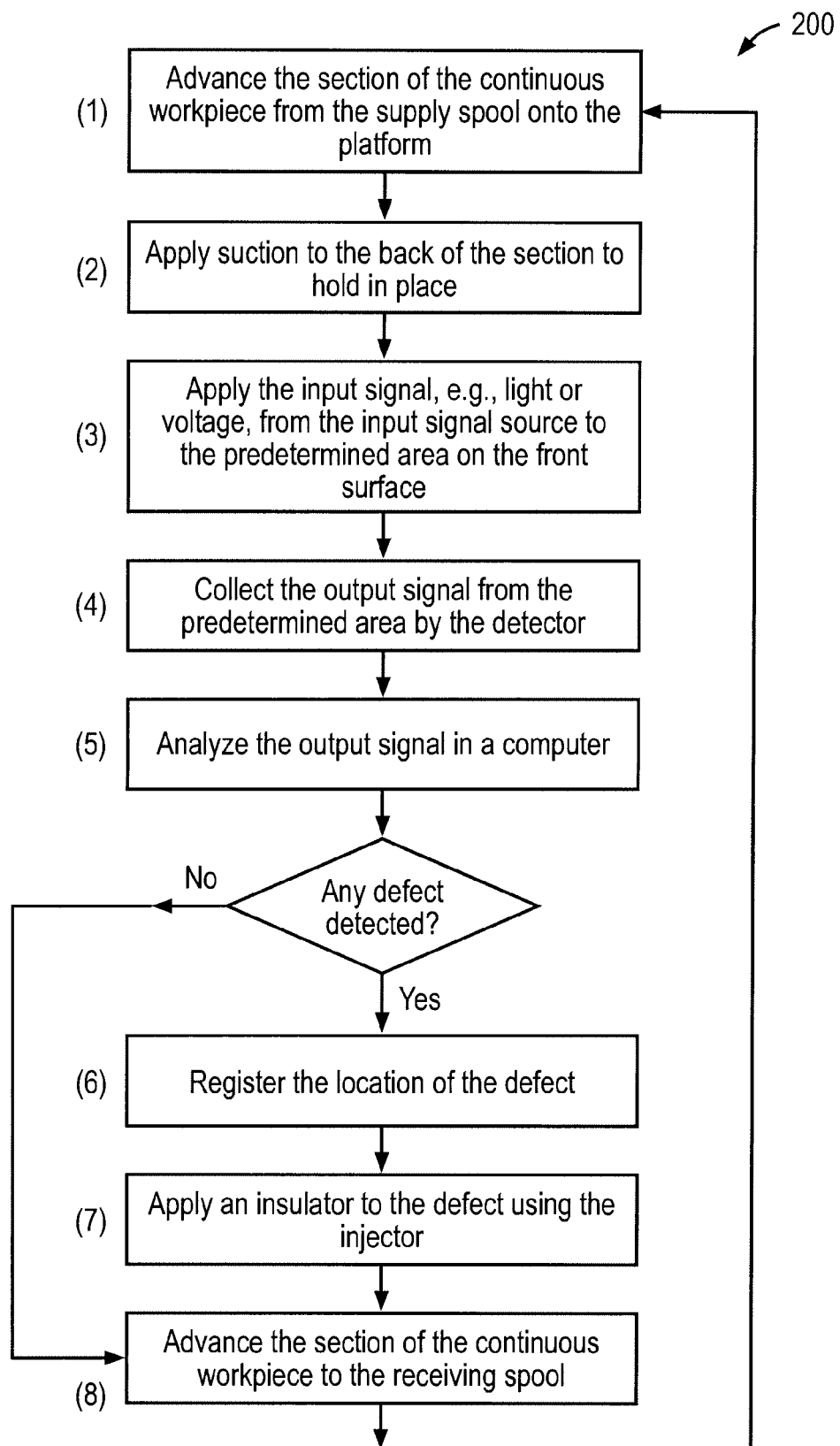
FIG. 9B shows an exemplary process flow using the defect detection tool shown in FIG. 9A.

FIG. 9B shows an embodiment of an exemplary detection process flow 200 using the system shown in FIG. 9A. In step (1), the section 94A of the continuous workpiece 94 is advanced from the supply spool to the surface of the platform 53. In step (2), suction is applied to the back surface of the section 94A so that the section of the continuous workpiece 94 can be made substantially flat and held in place. In step (3), the input signal is applied to a predetermined area on the front surface of the section. The predetermined area may be the area on which a finger pattern will be formed after the detection and passivation process. Alternatively, at this step the signal may be applied to the predetermined area when the predetermined area is at a detection location. In step (4), the detector 98 collects the output signal from the predetermined area, and in step (5), this data is analyzed using a computer. If no defect is detected process continues with step (8) in which the section 94A is advanced to the receiving spool, and the process restarts with a following section of the continuous workpiece. If a defect is detected, the process is followed with step (6) in which the position of the defect is registered, i.e., the defect's coordinates in the predetermined area is mapped and recorded in the computer's data base. Next, in step (7), using the position information of the defect, a moving mechanism controlled by the computer drives the injector 99 over the position of the defect to apply an insulating material to the defect. Alternatively, before the step (7), the predetermined area with the defect may be advanced into a passivation location on the platform 53 to apply the injector 99 while another predetermined area is being processed at the detecting location. After the defect is passivated, in step (8), the section is advanced to the receiving spool. It should be noted that the size of the subject defects may vary widely from a few microns up to 1 mm. The insulator dispensed by the injector on a defect region may be as wide as 1-2 mm or even more. It is preferred that the insulator be transparent. In this case, the current loss in the solar cell is minimized even if the insulator size is much larger than the defect size. For example, a 2 mm diameter insulator drop deposited on a 10 micrometer size defect would not cause any current loss due to the presence of insulator over the TCO layer provided that the insulator is substantially transparent to sunlight.

As mentioned before, it is also possible to integrate defect detection and passivation process with a finger pattern deposition step. In this case, the sections of the continuous workpiece that received defect detection and passivation steps may move to a screen printing/curing unit (not shown) of the overall system before the sections are advanced to the receiving spool.

Figure 10:
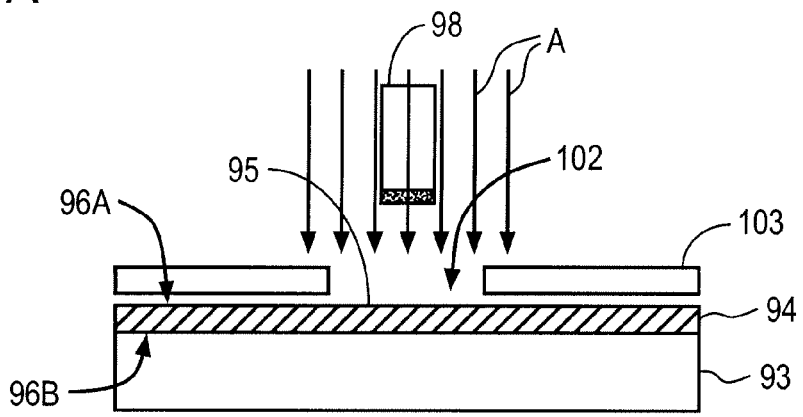
FIGS. 10-11 show various embodiments of the defect detection process and equipment.

It should be noted that the nature of the detector 98 depends on the defect detection method and the input signal source employed. The embodiments of the present invention may use both non-contact detection methods and contact detection methods. The non-contact defect detection methods may utilize techniques such as photoluminescence and infrared thermography. FIG. 10 schematically shows a detection area 95 and sections of the process platform 93 and workpiece 94 under the detection area 95. Both photoluminescence and IR thermography uses illumination, i.e., light photons, as the input signal which is depicted by arrows 'A'. In FIG. 10 the detection area 95 is defined by an opening 102 of a mask 103 placed over the front surface 96A of the workpiece 94. The back surface 96B of the workpiece 94 is on top of the process platform 93. In IR thermography the portion of the solar cell structure of the workpiece 94 within the detection area 95 is illuminated by light coming through the opening 102 of the mask 103 and impinging on the front surface 96A. The impinging light or input signal creates a voltage and a resulting current within the solar cell structure. Light generated current passes through any short circuits in the solar cell structure causing local heating in those locations. The detector 98 in this case is an IR camera which sees and records the heated regions or the short circuits as output signals. It should be noted that this technique can detect short circuits but cannot detect the defects that do not short the TCO layer to the back contact (defect region 27C in FIG. 2).

Another non-contact approach is photoluminescence process. In this case light is shone through the opening 102 of the mask 103 as the input signal and the detector 98 detects photoluminescence coming from the solar cell structure as the output signal. In this case all non-active regions, i.e., regions that do not generate photoluminescence, in the solar cell structure including shorted regions, open circuit regions and regions comprising foreign particles, etc. may be detected. As mentioned before, these techniques can be operated either in a DC or AC mode. In the latter case the excitation source or input source is modulated, and the images are acquired and processed to as to "lock-in" on the signal of interest, with a substantially improved signal to noise ratio. For the specific CIGS solar cell structure the non-contact detection method using photoluminescence is attractive because it avoids surface damage and can detect defects that are shorts as well as defects that may not be shorts but would create shorts when a finger pattern is deposited. It should be noted that the mask 103 may be in the shape of the predetermined grid region 81 of FIG. 8 to carry out detection and passivation only in this grid region.

Figure 11:
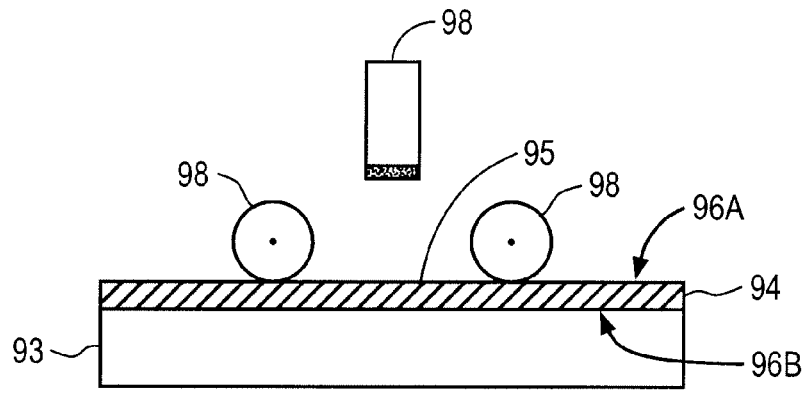

For contact detection methods, electrical contacts need to be made to the top and bottom electrodes of the solar cell structure to provide an input signal. An example is shown in FIG. 11 where the front surface 96A of the workpiece 94 is contacted by highly conductive top contacts 98 and the ohmic contact to the metallic back surface 96B of the workpiece 94 is made by the top surface of the process platform 93, which may be a metallic sheet. As shown in FIG. 11 the top contact 98 may comprise two or more conductive rollers which are placed on the front surface 96A of the workpiece 94. The area between the two conductive rollers 98 defines the detection area 95. The roller surface may also be coated with a conductive rubber material to reduce damage to the TCO surface. Although the contacts shown in FIG. 11 are rollers, other types of electrical contacts such as brushes, etc. may also be used.

Two exemplary detection methods, thermography and electroluminescence may use the conductive rollers to generate input signals. In thermography, a voltage is applied between the rollers and a bottom contact to the back surface 96B of workpiece 94. Short circuiting defect regions in the detection area 95 pass higher current than the rest of the device and therefore get hotter. An IR camera is used as the detector detects the IR radiation from the hot spots as the output signal. As described above, this technique can detect short circuits effectively. However, defects that do not pass high current in the solar cell structure may go undetected. The second exemplary contact method is electroluminescence where a voltage or input signal is applied between the rollers and a bottom contact to the back surface 96B of the workpiece 94 and an electroluminescence detector senses the radiation or the output signal coming from the detection area 95. Shorted areas, open circuited areas as well as areas containing foreign matter may be detected this way as dark, inactive regions of the cell structure. Therefore, electroluminescence detection is preferred for CIGS solar cell structures since it can detect defects that may not be shorts but would create shorts when a finger pattern is deposited.

In another embodiment of the present invention, the above described defect detection methods and techniques may be applied to a completed solar cell structure including a terminal, such as a grid pattern, on the front light receiving surface of the solar cell to detect efficiency reducing defects such as shunting defects. In context of this application, an efficiency reducing defect is the defect that electrically shorts or short circuits the back contact or the conductive substrate of the solar cell to a location which includes a particular portion of the grid pattern such that electrons (or electrical current) collected by the grid pattern leaks into that defect from that location and communicated to the back contact or conductive substrate. Such a leaky defect may be due to an ohmic shunt or it may also be due to a leaky diode at the location, i.e. the leakage current may be due to a weak or leaky diode characteristics at the location. The defect may be under or in very close proximity of the location so that it pairs itself electrically with this location by switching the direction of electron or current flow from the busbars to the defect, resulting in electron or current loss. Such locations surrounding the defect while including a portion of a grid pattern will be referred to as paired location hereinafter, i.e., the location that is electrically connected to the defect by delivering electrons or electrical current to the defect from that location. In this embodiment, after an efficiency reducing defect is detected by one of the methods described above, the negative effect of this defect on the cell is reduced by reducing the size of the paired location of this particular defect by a passivation process of the present invention without removing the defect from the solar cell. The passivation process generally involves reducing the size of the paired location by physically and electrically isolating the defect from the entire grid pattern or at least a portion of the grid pattern by cutting through the grid pattern and the whole device structure at locations close to the defect so as to inhibit unwanted electron or current flow into the defect from the parts of the grid pattern beyond the cuts made. As will be described more fully below, this may be done by forming a gap between the defect and the grid pattern, for example, by removing a segment of the solar cell including some grid pattern material if the defect is in proximity of the grid pattern. If the defect is in contact with a particular portion of the grid pattern, this particular portion is also physically and electrically separated from the rest of the grid pattern as the segment of the solar cell is removed. The material removal process may be physical cutting and it may be conducted in a cleaning solution to remove small dust or material pieces resulting from the removal process. The material removal process may be further conducted in a mildly acidic solution to dissolve small particles resulting from the process.

Figure 12A:
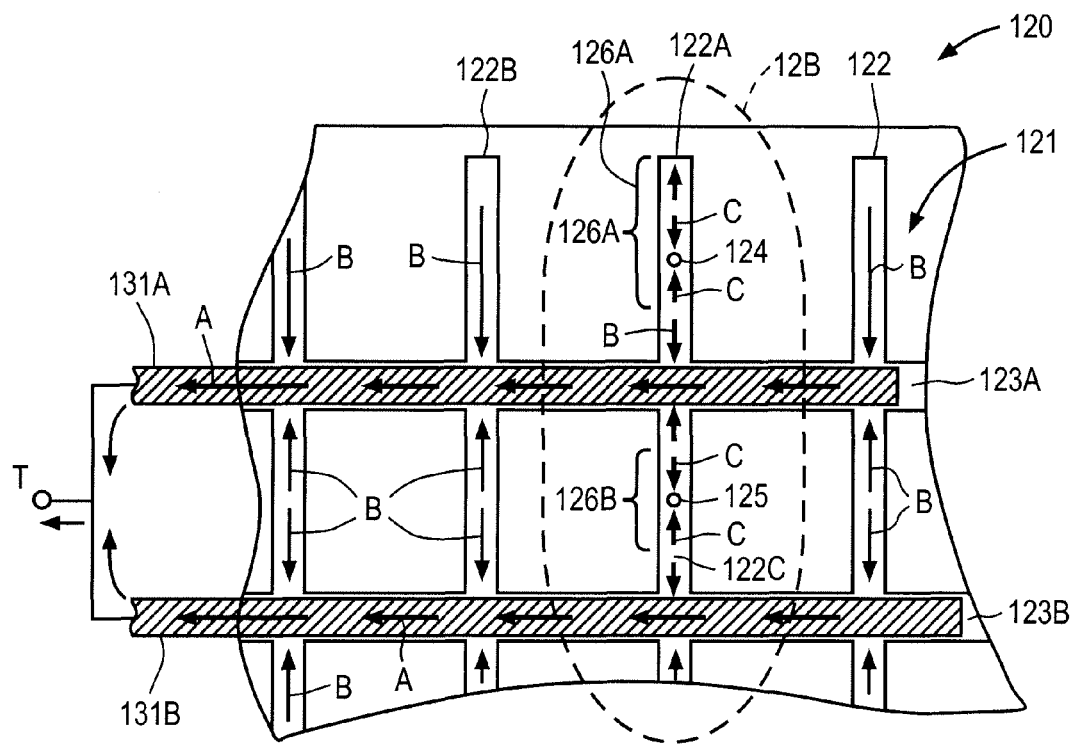
FIG. 12A shows a top plan view of a portion of a solar cell with two exemplary defects.

FIG. 12A shows a top (illuminated surface) view of a portion 120 of a solar cell structure with grid pattern, or a completed solar cell. The portion 120 of the completed solar cell comprises a grid pattern 122 formed on a top surface 121 of the solar cell. The grid pattern 122 includes exemplary fingers 122A, 122B that are marked (as well as other unmarked fingers), and two busbars 123A and 123B. Interconnect conductors 131A and 131B, which may be copper ribbons, are attached to the busbars 123A and 123B, or current collectors, respectively to conduct electron flow collected from the top surface 121 to a terminal point 'T'. The direction of the electron/current flow is depicted by arrows 'A'. It should be noted that the arrows 'A' may represent electron flow or current flow depending on the type of solar cell. In this example, the solar cell is a CIGS type solar cell fabricated on a flexible conductive substrate. Therefore, the terminal point 'T' is a negative terminal and the arrows 'A' represent an electron flow, which is reverse of the current flow.

There are two exemplary defects shown in FIG. 12A. The first defect 124 is shown under the finger 122A connected to the busbar 123A. The second defect 125 is shown under the finger 122C, which is between and connected to both of the busbars 123A and 123B. In this configuration, the first defect 124 is paired with the finger 122A through a first paired location 126A, and the second defect 125 is paired with the finger 122A through a second paired location 126B. The first and second defects 124, 125 are efficiency reducing defects which short the grid pattern 122 at the paired locations 126A and 126B to the conductive substrate underneath and cause electron leakage into the defects from the paired locations, thereby reducing the performance of the overall solar cell. In FIGS. 12A and 12B, top surfaces of the paired locations 126A and 126B, which are portions of the fingers 122A and 122C, are shown. In this respect, each of the first and second paired locations 126A and 126B may extend from the fingers 122A and 122C to the substrate of the solar cell (see FIG. 12C).

It should be noted that the lengths of the first paired location 126A and the second paired location 126B shown in FIG. 12A are arbitrarily chosen to demonstrate the point. In reality, the resistivity of the fingers 122A and 122C as well as the resistance through the defects 124 and 125 may be so low that the length of the first paired location 126A may be equal to the whole length of the finger 122A, and the length of the second paired location 126B may be the whole length of the finger 126B extending from the first busbar 123A to the second busbar 123B. In fact it is even possible that these defects may attract electron flow from the busbars, which means that the paired locations may extend into the busbars 123A and 123B. It should be noted that typical sheet resistance of the transparent conductive layers employed in such solar cell structures is in the range of 20-80 ohms/square, whereas this value is in the range of 5-20 milli ohms/square for the grid pattern deposited on the transparent conductive layer. Therefore, any current collected from the cell tends to flow through the grid pattern. If there is a low resistance shunting defect electrically connected to the grid, this defect may be able to attract current from a large portion of the grid due to the low resistance of the grid. Therefore, the paired locations, which signify the area of the grid that may provide leakage current to the defect, are usually much larger than what is depicted in FIG. 12A.

As shown in FIG. 12A, unlike fingers 122A and 122C, the fingers not paired with defects, such as finger 122B, have undisrupted and normal electron flow towards the busbars 123A and 123B, as depicted with arrows 'B'. However, in the fingers 122A and 122C, electrons flow towards the first and second defects 124 and 125 surrounded by the paired locations 126A and 126B, as depicted with arrows 'C', which represents a loss from the cell's performance.

Figure 1:
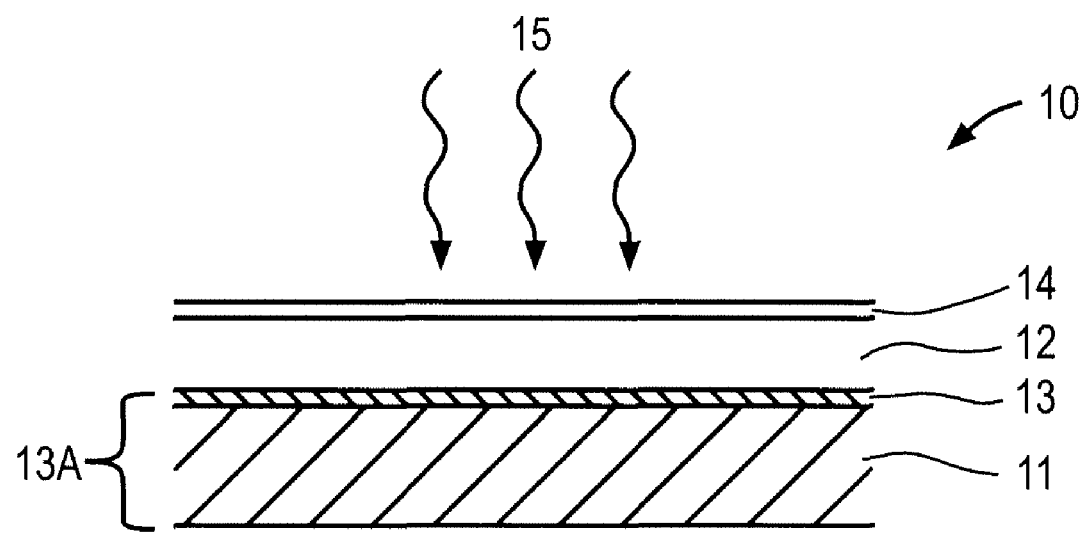
FIG. 1 is a cross-sectional view of an exemplary thin film solar cell employing a Group IBIIIAVIA absorber layer.

The completed solar cell of the top portion 120 shown in FIG. 12A may have a structure similar to the one shown in FIG. 1. The solar cell including the top portion 120 may comprise a substrate, a contact layer, an absorber layer (such as a CIGS type absorber layer), a transparent layer which may comprises a buffer layer (such as a sulfide compound layer like cadmium sulfide or indium sulfide) and a transparent conductive layer (such as a transparent conductive oxide like zinc oxide, indium tin oxide, iridium zinc oxide, etc.). Grid pattern is disposed on the transparent conductive layer. The completed solar cell is preferably a thin film solar cell and the substrate is a conductive foil substrate with a thickness typically smaller than 250 µm, preferably smaller than 100 µm. The conductive foil substrate may be made of metals and/or alloys comprising steel, stainless steel, molybdenum, titanium, copper, aluminum, etc. If the substrate is an insulating foil it may comprise a polymeric material such as polyimide. Kapton-type materials supplied by companies, such as DuPont, are suitable for this application. The first defect 124 and the second defect 125 under the fingers 122A and 122C may be holes or pinholes through which the finger material may electrically short to the contact layer and/or the substrate. It should be noted that grid patterns are highly conductive and they generally comprise silver metal. Various other types of defects such as those discussed with reference to FIG. 2 may also exist in the completed solar cell. The presence and the locations of the first defect 125 and the second defect 124 may be determined using the defect detection techniques discussed in the above embodiments.

As mentioned above, the first defect 124 and the second defect 125 reduce the performance of the completed solar cell. The shunt resistance introduced by such defects reduces the fill factor and thus the efficiency of the device. As discussed before, some prior art methods used chemical approaches to etch away or anodize at least one of the transparent conductive layer, the absorber layer or the contact layer of the solar cell at the exact location of the defect with the goal of passivating the defect. In another approach a laser was used to ablate the defective region. Yet another technique applied a physical tool such as a scriber on the defect with the goal of physically eliminating it. Such approaches do not yield good results for thin film solar cell structures, especially for devices employing compound semiconductor absorber layers constructed on conductive foil substrates. For example, a CIGS-type solar cell fabricated on a 25-100 µm thick metallic foil substrate, chemical etching or anodization methods do not work well because CIGS is made of Cu, In, Ga and Se and chemical or electrochemical etching of this compound material does not remove all these different materials at the same rate and leaves behind residues that may be conductive. Therefore, while removing a shorting defect, new shorts may be introduced in the device structure where the chemical or electrochemical etching process is performed. Furthermore, if the defect is under the grid pattern, etching techniques cannot be used because etching the grid, which is a thick layer, is not very practical. Mechanical processes that try to scratch away the defect may introduce even more defects, especially since the defect itself comprises highly conductive debris shorting the device. Physical scratching right on the defect may actually smear such conductive debris and often make the electrical shorting even worse in thin film solar cell structures.

In the following part of the description, a method of reducing or eliminating the influence of defects without disturbing the defects or removing the defects from the solar cell will be described in connection to FIGS. 12A and 12B. The method of the present invention passivates the effects of the first and second defects 124 and 125 by isolating the paired locations 126A and 126B without disturbing the defects. Disturbing the defects may cause additional shunting behavior as explained above. FIG. 12B shows the dotted region 12B from FIG. 12A in detailed top view after a passivation process. As shown in FIG. 12B, a first sacrificed portion 131 of the finger 122A, which is the upper portion of the first paired location, is electrically isolated by forming a first gap 132A between the first defect 124 and a remaining portion 134 of the finger 122A connected to the busbar 123A. Since the first defect 124 is physically and electrically separated from the body of the grid pattern 122, electron flow into the first defect 124 is limited to the size of the first sacrificed portion 131 of the first paired location 126A.

Figure 12C:
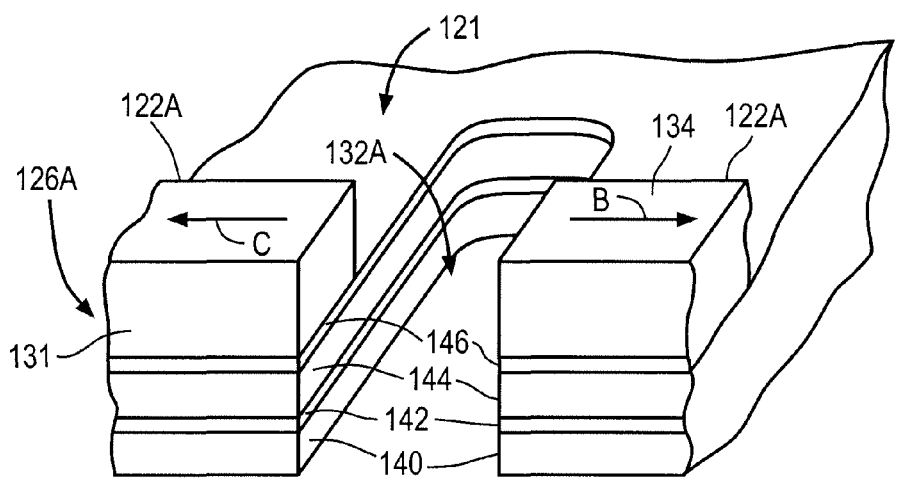
FIG. 12C shows a cutout cross sectional view taken along the line 12C-12C in FIG. 12B.
Figure 12B:
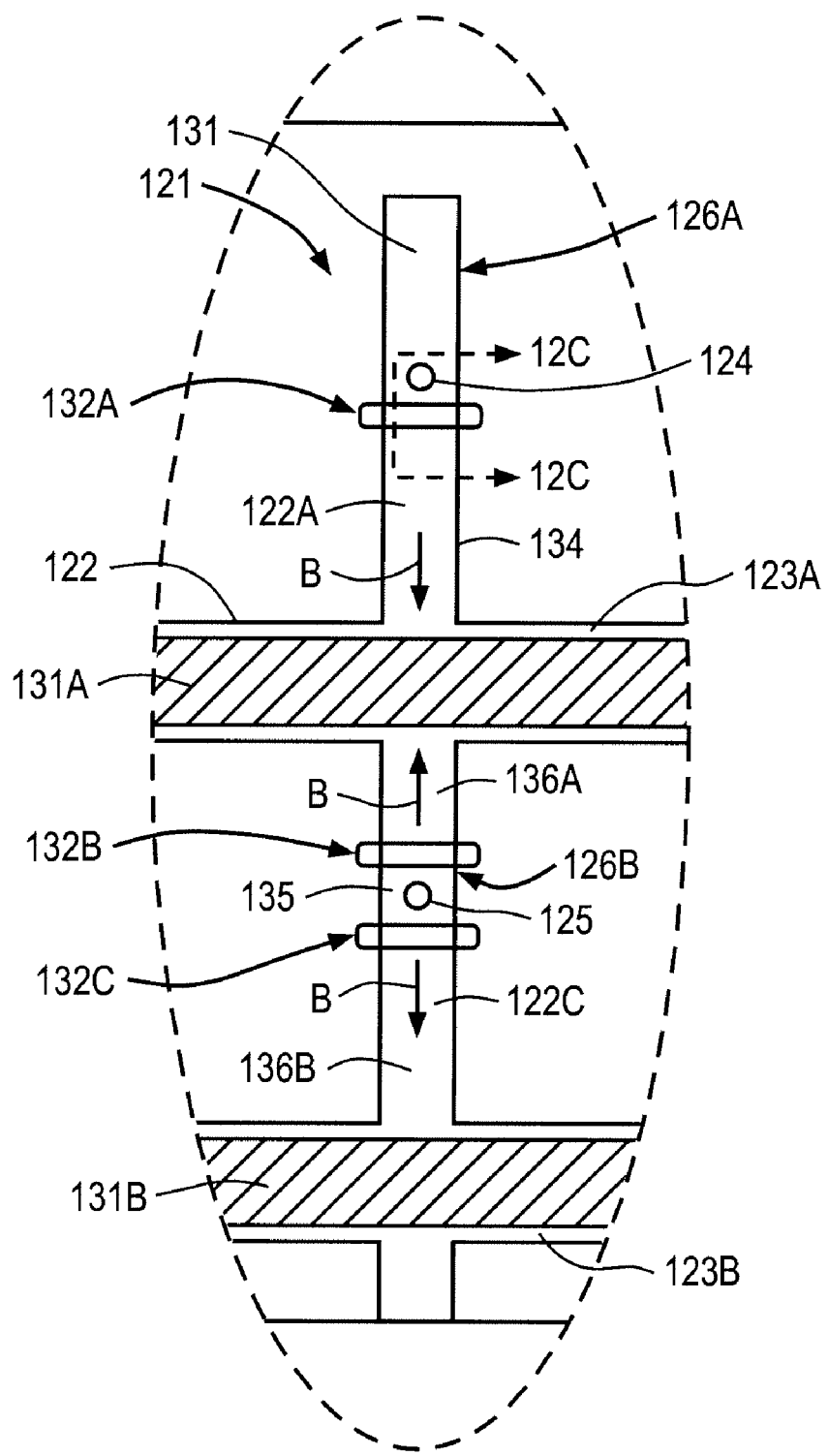
FIG. 12B shows a detailed view of a section marked 12B in FIG. 12A, wherein the defects have been passivated using the passivation process of the present invention.

FIG. 12C is a cutout cross sectional view taken along the line 12C-12C in FIG. 12B. As shown in FIG. 12C, the gap 132A or the hole is formed by cutting through the solar cell layers: substrate layer 140, contact layer 142, absorber layer 144, buffer-and-transparent conductive layers 46, and the first sacrificed layer portion 131 and the remaining portion 134 of the finger 122A. As also seen in FIG. 12C, the first paired location 126A (left side of the gap 132A on the paper) involves a three dimensional zone extending between the finger 122A and the substrate layer 140. Due to the gap 132A, electrons in the remaining section 134 of the finger 122A flows toward the busbar 123A in the direction of arrow 'B' and collected, while the electrons in the paired zone 126A flow towards the first defect 124 in the direction of arrow 'C'. Therefore in order to keep a larger portion of the finger 122A active and collecting current, the gap 132A is located close to the first defect 124. Electrons flowing into the first defect from the first sacrificial portion 131 of the finger 122A containing the first defect 124 still constitute a loss, however, this loss is substantially smaller than the case depicted in FIG. 12A.

Similarly, the second defect 125 is electrically separated from the busbars 123A and 123B by forming a second gap 132B and a third gap 132C on the finger 122C. The second defect 125 is located between two busbars 123A and 123B or current collectors. Therefore, the size of the paired location 126B can be substantially reduced by reducing the distance between the second gap 132B and the third gap 132C on two sides of the second defect 125. In this configuration, due to the second gap 132B, electrons in a first remaining section 136A of the finger 122C flow toward the busbar 123A; and due to the third gap 132C, electrons in a second remaining section 136B flow toward the busbar 123B. A second sacrificed portion 135 of the finger 122C, which is the upper portion of the second paired location 126B, is electrically isolated by forming the second and third gaps 132B and 132C. The second defect 125 is physically and electrically separated from the body of the grid pattern 122, and the electron flow into the second defect 125 is limited with the size of the second sacrificed portion 135 of the second paired location 126B. Therefore in order to keep a larger portion of the finger 122C active and contributing to the device efficiency, the second and third gaps are located close to the second defect 125. A preferred distance from the defects to the cuts may be in the range of 0.5-2 mm. It should be noted that the preferred method of forming the gaps 132A, 132B and 132C is removing the whole solar cell structures at these locations including the substrate. Therefore, the technique applies to thin film solar cells employing flexible substrates. Such removal can be achieved using tools such as cutting wheels, die cutters, stamping tools, etc., that cut through the whole solar cell structure including the front portion and the back portion, which includes the substrate.

The passivation process of the present invention may be used very efficiently with solar cells using a mesh grid pattern 200 comprising a network of fingers 202 formed on a solar cell surface 204. Current collected by the network of fingers 202, which is depicted by arrows, flows to a terminal 'T' which is electrically connected to the network of fingers.

Figure 13:
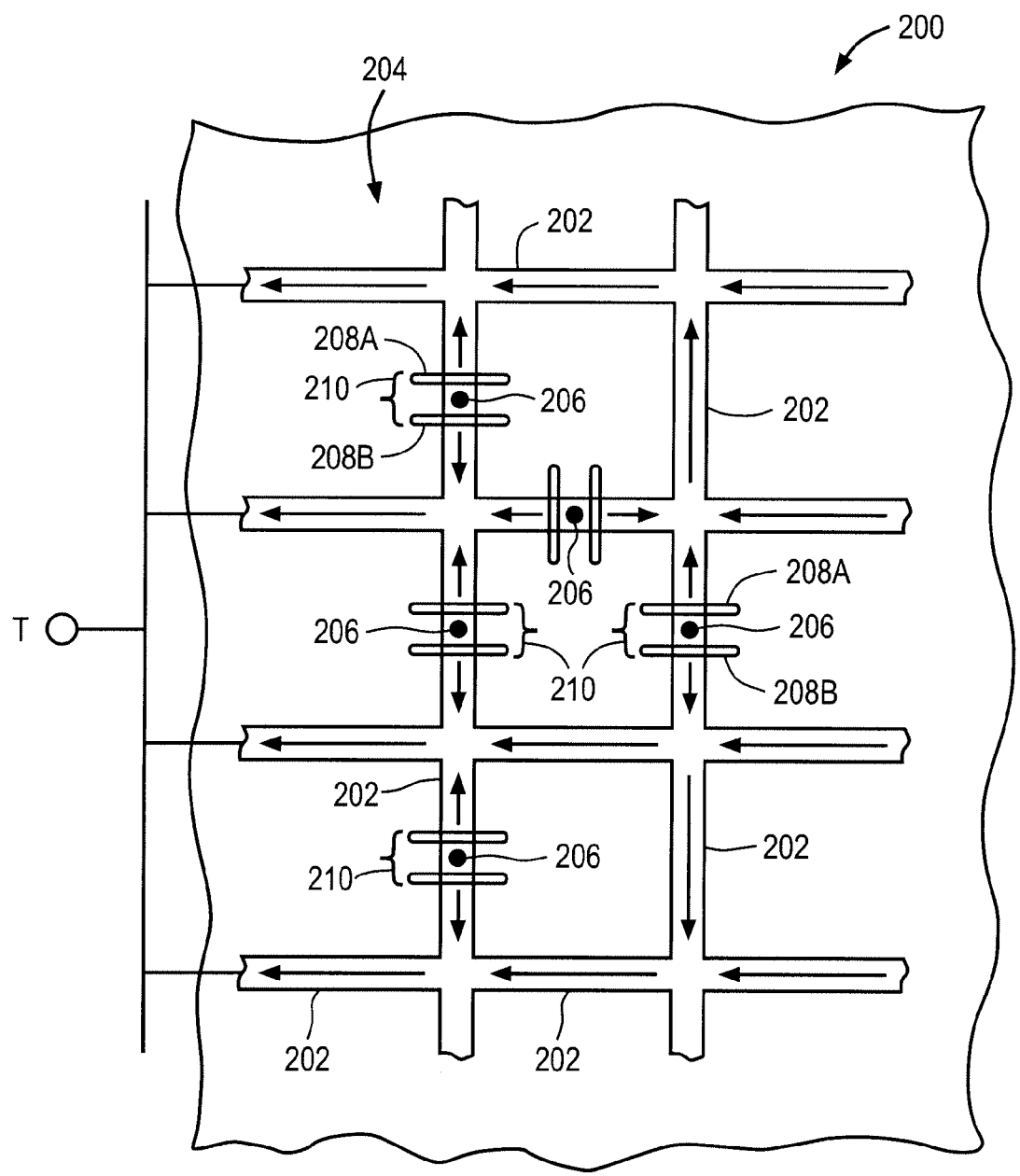
FIG. 13 shows in plan view a mesh grid pattern on a front side of a solar cell with passivated exemplary defects

Each defect 206 is passivated by forming two gaps or cuts, namely a first gap 208A and a second gap 208B to reduce the size of its respective paired location 210 as described above. As can be seen in FIG. 13, due to the mesh structure of the finger network, size of each paired location 210 can be significantly reduced, and the remaining portions of the fingers all contribute to the photogenerated current of the device because the collected current can always find a pathway through the remaining parts of the fingers to the terminal 'T'. This results in an increase in the usable finger area in the mesh grid pattern for current collection and an increase in the collected current, and therefore the efficiency of the device.

In a process sequence the locations of the defects are detected in a defect detection station and the passivation process is applied in a passivation station where the gaps may be formed using a cutting apparatus. The present invention may be carried out in batch mode involving the defect detection and position determination, and the passivation processes being carried out in batch mode on individual finished solar cells. Alternately, the defect detection and passivation steps may be carried out in a roll-to-roll manner before the solar cells are individually cut from a flexible workpiece. Furthermore, it is also possible that the defect detection and location determination may be carried out in a roll-to-roll manner and then the passivation process may be applied to the individual solar cells in batch mode after the individual solar cells are cut out of the roll of a continuous solar cell structure and separated from each other. The advantage of this last approach is the fact that the passivation step and the tool used for that operation may be simple to build and operate.

Although the present inventions are described with respect to certain preferred embodiments, modifications thereto will be apparent to those skilled in the art.

I claim:

1. A method of detecting and passivating at least one defect in a solar cell, comprising:
   providing the solar cell, the solar cell including a backside and a front light receiving side disposed over the backside, wherein the backside includes a substrate, and the front light receiving side includes a photovoltaic layer disposed over the substrate and a conductive grid with a plurality of conductive grid sections disposed over the photovoltaic layer, the conductive grid for collecting a current produced by the solar cell;
   detecting the at least one defect in the solar cell;
   determining an affected conductive grid section from the plurality of conductive grid sections associated with the at least one defect, wherein an undesired current leaks to the at least one defect from the affected conductive grid section of the conductive grid; and
   mechanically cutting out a segment of the solar cell including a first portion the affected conductive grid section and underlying portions of the photovoltaic layer and the substrate to electrically isolate the affected grid section from the conductive grid, wherein the step of mechanically cutting out a segment of the solar cell leaves a cavity extending between and including the front light receiving side and backside of the solar cell including the substrate.

2. The method of claim 1 wherein the step of mechanically cutting is performed in a solution.

3. The method of claim 1, wherein the photovoltaic layer includes an absorber film, a transparent conductive film formed over the absorber film, and wherein the absorber film is formed over a contact layer disposed on the substrate.

4. The method of claim 3 wherein the absorber film includes a Group IBIIIAVIA thin film semiconductor.

5. The method of claim 1, wherein the step of detecting is performed using illuminated lock-in thermography with a near IR illumination source.

6. The method of claim 1, wherein the step of mechanically cutting is performed by a punch that is laterally and longitudinally movable across the surface of the solar cell for accurate positioning over the segment of the solar cell, and wherein the punch mechanically cuts through the solar cell to remove the segment thereby isolating the affected grid section.

7. The method of claim 1 further comprising mechanically cutting out another segment of the solar cell including a second portion the affected conductive grid section and underlying portions of the photovoltaic layer and the substrate to electrically isolate the affected grid section, from the conductive grid, wherein the affected conductive grid section is located between the first portion and the second portion that are mechanically cut, and wherein the step of mechanically cutting out another segment of the solar cell leaves a cavity extending between and including the front light receiving side and backside of the solar cell including the substrate.

8. The method of claim 1, wherein the conductive grid includes busbars and conductive fingers.

9. The method of claim 4, wherein the substrate is a conductive foil.

10. The method of claim 9, wherein the conductive foil comprises one of steel, stainless steel, and aluminum.

11. The method of claim 10, wherein a contact layer including molybdenum and ruthenium is interposed between the absorber film and the substrate.

12. The method of claim 3, wherein the transparent conductive film comprises a buffer layer formed over the absorber film and a transparent conductive layer formed on the buffer layer, wherein the buffer layer includes one of cadmium sulfide and indium sulfide, and the transparent conductive layer includes one of zinc oxide, indium tin oxide and indium zinc oxide.

13. The method of claim 8, wherein the conductive grid comprises silver.

* * * * *